(12) United States Patent
Furuhashi et al.

(10) Patent No.: US 11,098,138 B2
(45) Date of Patent: Aug. 24, 2021

(54) PHOTOPOLYMERIZATION INITIATOR AND PHOTOCURABLE COMPOSITION

(71) Applicant: TOKUYAMA DENTAL CORPORATION, Tokyo (JP)

(72) Inventors: Koji Furuhashi, Tokyo (JP); Hironobu Akizumi, Tokyo (JP)

(73) Assignee: TOKUYAMA DENTAL CORPORATION, Tokyo (JP)

(*) Notice: Subject to any disclaimer, the term of this patent is extended or adjusted under 35 U.S.C. 154(b) by 478 days.

(21) Appl. No.: 16/078,000

(22) PCT Filed: Mar. 8, 2017

(86) PCT No.: PCT/JP2017/009248
§ 371 (c)(1),
(2) Date: Aug. 14, 2018

(87) PCT Pub. No.: WO2017/154983
PCT Pub. Date: Sep. 14, 2017

(65) Prior Publication Data
US 2021/0095055 A1    Apr. 1, 2021

(30) Foreign Application Priority Data
Mar. 9, 2016    (JP) .............................. JP2016-045523

(51) Int. Cl.
| | | |
|---|---|---|
| *C08F 2/46* | (2006.01) | |
| *C08F 2/50* | (2006.01) | |
| *C08G 61/04* | (2006.01) | |
| *A61K 6/62* | (2020.01) | |
| *C08K 3/22* | (2006.01) | |
| *C08K 3/36* | (2006.01) | |

(52) U.S. Cl.
CPC ................. *C08F 2/50* (2013.01); *A61K 6/62* (2020.01); *C08K 3/22* (2013.01); *C08K 3/36* (2013.01); *C08K 2003/2241* (2013.01); *C08K 2003/2244* (2013.01)

(58) Field of Classification Search
CPC ............... C08F 2/06; C08F 2/50; C08G 61/04
USPC ........... 522/48, 47, 6, 189, 184, 1, 71; 520/1
See application file for complete search history.

(56) References Cited

U.S. PATENT DOCUMENTS

| | | | |
|---|---|---|---|
| 3,729,313 A | 4/1973 | Smith | |
| 3,741,769 A | 6/1973 | Smith | |
| 3,808,006 A * | 4/1974 | Smith | ..................... G03F 7/031 |
| | | | 430/495.1 |
| 4,386,154 A | 5/1983 | Smith | |
| 4,518,676 A | 5/1985 | Irving | |
| 5,545,676 A | 8/1996 | Palazzotto | |
| 6,017,660 A | 1/2000 | Palazzotto | |
| 6,084,004 A | 7/2000 | Weinmann | |
| 6,187,836 B1 | 2/2001 | Oxman et al. | |
| 6,331,080 B1 | 12/2001 | Cole | |
| 2001/0055726 A1 | 12/2001 | Kanna | |
| 2004/0180983 A1 | 9/2004 | Hara et al. | |
| 2008/0009557 A1 | 1/2008 | Feng | |
| 2009/0005469 A1 | 1/2009 | Craig et al. | |
| 2011/0172323 A1 | 7/2011 | Akizumi et al. | |
| 2012/0059079 A1 | 3/2012 | Fujinami et al. | |
| 2017/0014544 A1 | 1/2017 | Coqueret | |
| 2020/0069534 A1 * | 3/2020 | Furuhashi | ................ A61K 6/76 |

FOREIGN PATENT DOCUMENTS

| | | |
|---|---|---|
| CN | 1295455 A | 5/2001 |
| CN | 1537870 A | 10/2004 |
| CN | 101351182 A | 1/2009 |
| CN | 101477309 A | 7/2009 |
| CN | 102037024 A | 4/2011 |
| CN | 104940027 A | 9/2015 |
| JP | S5998103 A | 6/1984 |
| JP | S63273602 A | 11/1988 |
| JP | H111130945 A | 5/1999 |
| JP | 2001318464 A | 11/2001 |
| JP | 2002527566 A | 8/2002 |
| JP | 2005-213231 * | 8/2005 |
| JP | 2005-213231 A | 8/2005 |
| JP | 2007-231210 A | 9/2007 |
| JP | 2009542724 A | 12/2009 |
| JP | 4841973 B2 | 12/2011 |
| WO | 2015087020 A1 | 6/2015 |

OTHER PUBLICATIONS

Hara et al, JP 2005-213231 Machine Translation (Year: 2005).*
European Search Report dated Jul. 2, 2020 issued in the corresponding European Patent Application No. 17763323.7.
Perrin, "Ionisation Constants of Inorganic Acids and Bases in Aqueous Solution", p. 112, Jan. 1982, Elsevier Science & Technology; Cited in European Search Report.
European Search Report dated Sep. 24, 2019, Application No. EP17763323, 8 pages.
Chinese Office Action (CNOA) dated Sep. 29, 2020 issued in the corresponding Chinese patent application No. 201780011740.7 and its English translation.
International Search Report dated May 9, 2017 filed in PCT/JP2017/009248.

* cited by examiner

*Primary Examiner* — Jessica Whiteley
(74) *Attorney, Agent, or Firm* — Rankin, Hill & Clark LLP

(57) ABSTRACT

A photopolymerization initiator including (a) a photosensitizer, (b) a tertiary amine compound and (c) an aryliodonium salt wherein, as the aryliodonium salt (c), there is selected the one that generates an acid having a dissociation constant of not less than −3.0 in water of 25° C.

9 Claims, No Drawings

PHOTOPOLYMERIZATION INITIATOR AND PHOTOCURABLE COMPOSITION

TECHNICAL FIELD

This invention relates to a photopolymerization initiator and a photocurable composition containing the photopolymerization initiator which are useful for the dental materials, photoresist materials, printing and plate-making materials, and hologram materials, and are particularly useful for the dental materials.

BACKGROUND ART

Photopolymerization initiators that generate radicals or ion species upon the irradiation with light have been used in a variety of applications as photocurable compositions being combined with polymerizable unsaturated compounds or polymerizable cyclic compounds.

As photopolymerization initiators of this kind, there have been used photosensitizers that generate energy upon absorbing light and generate polymerization activating species using the generated energy. There have also been used reducing agents (electron donors) having a polymerization accelerating function in combination with the photosensitizers.

As the photosensitizers, there have been known acylphosphine oxide compounds and α-diketone compounds.

Specifically, the α-diketone compounds exhibit a radical-generating capability in a wavelength region of visible light that little affects the human body, and have been widely used in the field of, particularly, dental materials. For example, a camphorquinone which is a representative compound of the α-diketone is a yellow compound having a maximum absorption wavelength of 468 nm.

Further, as the photosensitizers, there have been known various coloring matters.

As for the reducing agents, furthermore, the amine compound is a representative example. In particular, a tertiary amine has been widely used in combination with the α-diketone.

In the field of the dental materials, the above-mentioned photopolymerization initiator is added to a paste-like composition (called composite resin) which chiefly comprises a polymerizable monomer and a filler so that the composite resin is imparted with the photopolymerizable capability. The composite resin in the state of paste is formed into the shape of a tooth. The thus formed composite resin is then cured by being irradiated with light from a dedicated light irradiator. Hereinafter, the light irradiated for polymerization and curing is often referred to as "active light".

In general, the active light is irradiated by using a light source of an output or light intensity of about 100 to 1500 mW/cm$^2$ in a wavelength region (chief absorption region of the α-diketone) of about 360 to 500 nm and from a distance of about not more than 10 mm.

In a dental clinic, for example, the composite resin is filled in a cavity of a tooth that is to be restored and is formed in the shape of the tooth. Thereafter, by using the dedicated light irradiator, the composite resin is irradiated with the active light, and is polymerized and cured to restore the tooth. In a dental laboratory, further, the composite resin is applied onto a plaster model in the shape of a tooth that is to be restored and is polymerized and cured by being irradiated with light. The thus cured body is then brought to the dental clinic where it is adhered to the tooth by using a dental adhesive to thereby restore the tooth.

When the photopolymerization initiator contains a photosensitizer like the α-diketone compound and the tertiary amine compound in combination, however, there remains a problem in that the viscosity of the composite resin (paste) increases while the composite resin is being filled or applied and makes it difficult to continue the operation.

That is, in filling or applying the paste, the practicing person needs to watch and judge the shape of the paste and the color tone of the cured body obtained by polymerizing the paste. This kind of operation is carried out in the dental light that illuminates the interior of the oral cavity or in the white light irradiated from the room light (e.g., fluorescent light). The light of this kind is called environmental light.

The environmental light, in general, has been adjusted to be about 500 to 10,000 lux by taking legibility into account. Though also dependent upon the light source, the intensity of the environmental light is not more than 1 mW/cm$^2$ in the chief absorption region (360 to 500 nm) of the α-diketone compound, and is less than several percent of the active light. Here, however, the polymerization initiator which comprises a combination of the α-diketone compound and the tertiary amine compound exhibits a good polymerizing activity responsive to the light in the visible region. Due to its good polymerizing activity, therefore, the polymerization initiator sharply responds to even the above-mentioned environmental light and starts curing. Therefore, if the operation is carried out in the environmental light which is indispensable for carrying out the operation of filling or application, then the high polymerizing activity becomes disadvantageous since it permits the paste to be gradually cured and causes the problem as described above.

The phenomenon of an increase in the viscosity of the paste during the operation such as filling or application can be avoided by decreasing the amount of the photopolymerization initiator that is added or increasing the amount of the polymerization inhibitor that is added. With these methods, however, the paste is not cured to a sufficient degree despite it is irradiated with the active light for a period of time comparable to the customarily employed period of time often arousing such problems that the strength of the obtained cured body decreases and the unpolymerized monomer remains much near the surface of the cured body. To have the paste polymerized and cured to a sufficient degree, therefore, the active light must be irradiated for extended periods of time. However, the composite resin is in many cases used in the oral cavity of a patient. Therefore, extending the irradiation time means that the operation is carried out requiring extended periods of time and, besides, forcing the patient to bear an increased amount of burden. Therefore, it has been desired to shorten the irradiation time (curing time).

Further, even by using the composite resin (paste) having improved stability in the environmental light by adding the photopolymerization initiator in a decreased amount, it is possible to shorten the curing time and to improve the strength of the cured body by increasing the intensity of the active light. Increasing the intensity of light, however, requires an increased amount of energy. Besides, even the visible light, if it is too intense, could cause damage to the human body and, specifically, to the eyes. Moreover, the light source that emits intense light, usually, generates much heat, too, and, therefore, might cause damage to the living body due to the heat. In recent years, for instance, there has been developed a source of active light that consumes less energy, opening the way to a widespread use of light irradiators using a laser diode and irradiating the light of an intensity of about 20 to 100 mW/cm$^2$.

Namely, with the method of adding the photopolymerization initiator in decreased amounts, it is not possible to shorten the curing time or to improve the strength of the cured body by using the light irradiator such as the laser diode. It is, therefore, difficult to carry out the polymerization and curing quickly and to a sufficient degree without causing burden to the patient.

By using the conventional photopolymerization initiators as described above, there has not yet been provided any composite resin that does not decrease its reactivity to the active light, that excels in its stability against the environmental light and that quickly undergoes the curing when it is irradiate with strong light from a dental light irradiator.

A patent document 1 proposes a photopolymerization initiator containing an aryliodonium salt, a photosensitizing compound and an electron donor compound.

A composite resin blended with the above photopolymerization initiator can be polymerized and cured requiring a shorter active light irradiation time than those of the conventional composite resins. However, the degree of shortening the active light irradiation time is not still sufficient, and it has been desired to further shorten the active light irradiation time (polymerizing/curing time). When the above photopolymerization initiator is used, further, there is seen no much improvement in the stability in the environmental light. To improve the stability in the environmental light, means is necessary such as adding the photopolymerization initiator in a decreased amount. As a result, therefore, the paste is less polymerized or cured despite it is irradiated with the active light. In fact, the above patent document 1 is not studying the stability or the like in the environmental light.

Further, the aryliodonium salt has been disclosed not only in the patent document 1 but also in patent documents 2 and 3. However, none of these patent documents are studying the stability in the environmental light or are closely studying about how the polymerizing activity would be affected depending on the kind of the aryliodonium salt.

PRIOR ART DOCUMENTS

Patent Documents

Patent document 1: JP-A-63-273602
Patent document 2: U.S. Pat. No. 3,729,313
Patent document 3: U.S. Pat. No. 3,741,769

OUTLINE OF THE INVENTION

Problems that the Invention is to Solve

An object of the present invention is to provide a photopolymerization initiator which exhibits excellent sensitivity to the active light, is capable of causing a polymerizable monomer to be quickly and completely polymerized and cured and is also capable of securing the stability in the environmental light, and a photocurable composition blended with the photopolymerization initiator.

Another object of the present invention is to provide a photocurable composition that can be favorably used as a dental composite resin.

Means for Solving the Problems

Through extensive experiment and study concerning the reactivity of the photopolymerization initiators to the active light, the present inventors have selected a specific aryliodonium salt and have used the aryliodonium salt in combination with a photosensitizer and a tertiary amine compound. The inventors have then discovered the fact that a very improved sensitivity is exhibited to the active light and have prepared a photocurable composition that remains stable in the environmental light as a result of utilizing the above properties. Based upon the above discovery, the present invention was completed.

According to the present invention, there is provided a photopolymerization initiator including (a) a photosensitizer, (b) a tertiary amine compound and (c) an aryliodonium salt wherein, as the aryliodonium salt (c), there is selected the one that generates an acid having a dissociation constant of not less than −3.0 in water of 25'C.

In the photopolymerization initiator of the present invention, the following embodiments are preferably employed:
(1) The aryliodonium salt (c) is a diphenyliodonium-2-carboxylate monohydrate;
(2) The photosensitizer (a) is an α-diketone;
(3) The tertiary amine compound (b) includes an aromatic tertiary amine (b1);
(4) The tertiary amine compound (b) includes the aromatic tertiary amine (b1) and an aliphatic tertiary amine (b2);
(5) The tertiary amine compound (b) is included in an amount of 10 to 1000 parts by mass and the aryliodonium salt (c) is included in an amount of 10 to 2000 parts by mass per 100 parts by mass of the photosensitizer (a); and
(6) The aryliodonium salt (c) is included in an amount of 10 to 80% by mass on the basis of the total amount of the tertiary amine compound (b) and the aryliodonium salt (c).

According to the present invention, further, there is provided a photocurable composition including the photopolymerization initiator and a polymerizable monomer.

In the above photocurable composition, it is desired that:
(1) A radically polymerizable monomer is used as the polymerizable monomer;
(2) The photopolymerization initiator is added in such an amount that the amount of the photosensitizer (a) in the photopolymerization initiator is 0.01 to 10 parts by mass per 100 parts by mass of the polymerizable monomer; and
(3) The photocurable composition, further, includes a filler, and is used as a dental composite resin.

Effects of the Invention

The photopolymerization initiator of the present invention includes (a) a photosensitizer, (b) a tertiary amine compound and (c) an aryliodonium salt. Here, a particularly important feature resides in that, as the aryliodonium salt (c), there is used a compound that generates an acid having a dissociation constant of not less than −3.0 in water of 25° C. Though the aryliodonium salt is a compound known as a photo acid generating agent, the specific aryliodonium salt used in the present invention generates an acid of a low acidity (i.e., having a dissociation constant of not less than −3.0 in water at 25° C.) through the cleavage reaction (polymerization reaction) upon the irradiation with the light. As a result, the aryliodonium salt has a very improved sensitivity to the active light. For instance, when there is used an aryliodonium salt that generates an acid having a high acidity, there is not obtained a high sensitivity to the active light.

That is, the photocurable composition blended with the photopolymerization initiator of the present invention exhibits improved sensitivity to halogen lamps, xenon lamps or lighting fixtures equipped with laser diodes (i.e., to the active light). Therefore, the photocurable composition cures very quickly.

The photocurable composition of the present invention exhibits a high sensitivity to the active light probably because the acid generated from the aryliodonium salt has such a low acidity that the neutralization reaction with the tertiary amine compound (b) is suppressed, and the polymerization is promoted to a sufficient degree due to the reducing property (electron donating property) of the compound.

Moreover, what is important is that since the photopolymerization initiator exhibits a high sensitivity to the active light as described above, it becomes easy to obtain the photocurable composition that has stability in the environmental light.

That is, the stability in the environmental light can be improved by decreasing the amount of the photopolymerization initiator (specifically, photosensitizer) that is added. By using the conventional polymerization initiators, however, if their amount is decreased, then the sensitivity to the active light decreases, as a matter of course, and an extended period of time is needed for the polymerization and curing. By using the photopolymerization initiator of the present invention having a very high sensitivity to the active light, on the other hand, the polymerization and curing upon the irradiation with the active light can be effectively prevented from decreasing despite the photopolymerization initiator is added in a decreased amount. Therefore, the polymerization and curing can be completed by the irradiation with the active light for only a short period of time.

With the photocurable compositions blended with the photopolymerization initiator of the present invention as demonstrated, for example, in Examples appearing later, it is allowed to so adjust the amounts of the components that a time of not shorter than 85 seconds and, specifically, not shorter than 90 seconds is needed before the photocurable composition starts polymerizing under the irradiation with the environmental light of an intensity of 0.3 mW/cm$^2$ on the surface of irradiation without accompanied by a decrease in the polymerizability or the curability upon the irradiation with the active light.

Therefore, when used as, for example, a dental composite resin, the photocurable composition of the invention facilitates the work such as filling the composition in the cavity of a tooth or applying the composition in the form of the tooth. Besides, upon irradiated with the active light for only a short period of time, the photocurable composition forms a cured body thereof having excellent properties such as strength, etc. and helps reduce the burden exerted on a patient.

MODES FOR CARRYING OUT THE INVENTION

<Photopolymerization Initiator>

The photopolymerization initiator of the present invention contains, as essential components, (a) a photosensitizer, (b) a tertiary amine compound and (c) an aryliodonium salt and may, further, contain suitable additives in a range in which they do not impair the photopolymerization initiation properties thereof.

(a) Photosensitizer;

The photosensitizer (a) used in the invention is a compound that generates energy upon absorbing light, generates active species like radicals effective for the polymerization due to the movement of energy (or due to the movement of electrons), and has a maximum absorption wavelength at 350 to 700 nm As the photosensitizer (a), there can be used known photosensitizers such as ketone compound (specifically, α-diketone compound), cumarin type pigment, cyanine type pigment, merocyanine type pigment, thiazine type pigment, azine type pigment, acridine type pigment, xanthene type pigment, squarium type pigment and pyrylium salt type pigment.

Among the above-mentioned photosensitizers, described below are concrete examples that can be favorably used.
Ketone Compounds:
Camphorquinone,
9,10-Phenanthrenequinone,
Benzyl,
Diacetyl,
Acetylbenzoyl,
2,3-Pentadione,
2,3-Octadione,
4,4'-Dimethoxybenzyl,
Acenaphthenequinone,
4,4-Bis(dimethylamino)benzophenone,
9-Fluorenone,
3,4-Benzo-9-fluorenone,
2-Dimethylamino-9-fluorenone,
2-Methoxy-9-fluorenone,
2-Chloro-9-fluorenone,
2,7-Dichloro-9-fluorenone
2-Nitro-9-fluorenone,
2-Acetoxy-9-fluorenone,
Benzanthrone,
Anthraquinone, and
2,4-Dihydroxybenzophenone.
Cumarine Type Coloring Matters:
3-Thienoylcumarin,
3-(4-Methoxybenzoyl)cumarin,
3-(4-Cyanobenzoyl)cumarin,
3-Thienoyl-7-methoxycumarin,
3-Benzoyl-7-methoxycumarin,
5,7-Dimethoxy-3-(4-methoxybenzoyl)cumarin,
3-Acetyl-7-dimethylaminocumarin,
7-Diethylamino-3-(4-cyanobenzoyl)cumarin,
7-Diethylamino-3-(4-dimethylaminobenzoyl)cumarin,
3-Cinnamoyl-7-diethylaminocumarin,
3-Carboxy-7-diethylamnocumarin,
3-(4-Carboxybenzoyl)-7-diethylaminocumarin,
3,3'-Carbonylbis(7-diethylamino)cumarin,
2,3,6,7-Tetrahydro-1,1,7,7-tetramethyl-10-benzothiazoyl)-11-oxo-1H,5H,11H-[1-benzopyrano [6,7,8-ij]quinoridine,
3,3'-Carbonylbis(5,7-)dimethoxy-3,3'-biscumarine,
3-(2'-Benzoxazoyl)-7-diethylaminocumarin,
3-(5'-Phenylthiazoyl-2')-7-diethylaminocumarin, and
3,3'-Carbonylbis(4-cyano-7-diethylamino)cumarin.
Cyanine Type Coloring Matters:
1,3,3,1',3,3'-Hexamethyl-2,2'-indocyanine perchlorate,
1,3'-Diethyl-2,2'-quino-selenacyanine iodide,
1,1'-Diethyl-2,4'-quinocyanine iodide,
3,3'-Diethyl-2,2'-thiazolynocarbocyanine iodide,
3,3',9-Triethyl-5,5'-diphenyl-2,2'-oxacarbocyanine iodide,
3,3'-Diethyl-2,2'-thiacarbocyanine iodide,
1,1'-Diethyl-2,4'-quinocarbocyanine iodide,
3,3'-Diethyl-2,2'-oxadicarbocyanine iodide,
3,3'-Diethyl-2,2'-(4,5,4',5'-dibenzo)thiadicarbo-cyanine iodide, and
3,3'-Diethyl-2,2'-oxatricarbocyanine iodide.
Melocyanine Type Coloring Matters:
3-Ethyl-5-[2-(3-methyl-2-thiazolidinylidene) ethylidene]-2-thio-2,4-oxazolidenedione, 3-Carboxymethyl-5-[2-(3-ethyl-2-benzothiazolinylidene)
ethylidene]rhodanine, and
3-Ethyl-5-[2-(3-ethyl-4-methyl-2-thiazolinylidene) ethylidene] rhodanine.
Thiazine Type Coloring Matters:
Methylene blue, and
Thionine chloride.
Azine Type Coloring Matters:
Riboflavin, and
1-Amino-4-nitrophenadine.
Acridine Type Coloring Matters:
1-Aminoacridine,
9-(2'-Hydroxystyryl)acridine,
Acryl orange, and
Acridine yellow.
Xanthene Type Coloring Matters:
Rhodamine,
Fluorescein, and
Rose Bengale.
Squalium Type Coloring Matters:
Dihydro-3-[2-hydroxy-3-(5-isopropyl-3,8-dimethyl-1-azirenyl)-4-oxo-2-cyclobutene-1-iridine]-7-isopropyl-1,4-dimethylazulenium hydroxide.
Pyrylium Salt Type Coloring Matters:
Triphenylpyrylium perchlorate, and
2,6-Bis(4-methylphenyl)-4-(4-phenylthiochloro-perchlorate.

In the present invention, the above-mentioned photosensitizers can be used each in a single kind or can be used in a combination of two or more kinds.

Among the above-mentioned photosensitizers, the most preferably used α-diketone compounds are camphorquinone, 9,10-phenanthrenequinone, benzyl, diacetyl, acetylbenzoyl, 2,3-pentadione, 2,3-octadione, 4,4'-dimethoxybenzyl and acenaphthenequinone.

(b) Tertiary Amine Compounds;

The tertiary amine compound (b) used in the present invention is a so-called reducing agent (or an electron donor) and works to promote the polymerization.

As the tertiary amine compound (b), there can be used either an aromatic tertiary amine (b1) having an aromatic ring in the molecules thereof or an aliphatic tertiary amine (b2) without aromatic ring in the molecules thereof.

A typical example of the aromatic tertiary amine (b1) is represented by the following general formula (1),

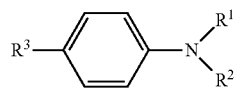

(1)

wherein, $R^1$ and $R^2$ are, independently from each other, alkyl groups, and $R^3$ is an alkyl group, an aryl group, an alkenyl group, an alkoxy group or an alkyloxycarbonyl group.

As the alkyl groups represented by $R^1$, $R^2$ and $R^3$, there can be exemplified those having 1 to 6 carbon atoms, such as methyl group, ethyl group, n-propyl group, i-propyl group, n-butyl group and n-hexyl group.

These alkyl groups may have a substituent, as a matter of course. As the substituent, there can be exemplified halogen atoms such as fluorine atom and the like atoms, as well as a hydroxyl group. For instance, $R^1$ to $R^3$ may be halogenoalkyl groups such as fluoromethyl groups or 2-fluoroethyl groups, or may be hydroxyalkyl groups such as 2-hydroxyethyl groups or the like groups.

As for the group $R^3$, further, the aryl group may be the one having 6 to 12 carbon atoms, such as phenyl group, p-methoxyphenyl group, p-methylthiophenyl group, p-chlorophenyl group or 4-biphenylyl group.

As the alkenyl group, there can be exemplified those having 2 to 12 carbon atoms, such as vinyl group, allyl group and 2-phenylethenyl group.

As the alkoxy group, there can be exemplified those having 1 to 10 carbon atoms, such as methoxy group, ethoxy group and butoxy group.

As the alkyloxycarbonyl group, there can be exemplified those of which the alkyloxy portion has 1 to 10 carbon atoms, such as methoxycarbonyl group, ethoxycarbonyl group, butoxycarbonyl group, amyloxycarbonyl group and isoamyloxycarbonyl group.

In the aromatic tertiary amine of the above general formula (1), $R^1$ and $R^2$ are, preferably, alkyl groups having 1 to 6 carbon atoms and, more preferably, are unsubstituted alkyl groups having 1 to 3 carbon atoms (e.g., methyl groups, ethyl groups or n-propyl groups) or 2-hydroxyethyl groups.

Further, $R^3$ is, preferably, an alkyloxycarbonyl group.

In the invention, the following compounds are most desirably used as the aromatic tertiary amine represented by the above general formula (1).
Methyl p-dimethylaminobenzoate,
Ethyl p-dimethylaminobenzoate,
Propyl p-dimethylaminobenzoate,
Amyl p-dimethylaminobenzoate,
Isoamyl p-dimethylaminobenzoate,
Ethyl p-diethylaminobenzoate, and
Propyl p-diethylaminobenzoate.

In the present invention, further, the following aromatic tertiary amines can also be favorably used though not represented by the above general formula (1).
N,N-Dimethylaniline,
N,N-Dibenzylaniline,
N,N-Dimethyl-p-toluidine,
N,N-Diethyl-p-toluidine, and
N,N-Di(β-hydroxyethyl)-p-toluidine.

As the tertiary amine compound (b), further, the invention can favorably use the following aliphatic tertiary amines (b2).
Triethanolamine,
N-Methyldiethanolamine,
Triethylamine,
Tributylamine,
N,N-Dimethylaminoethyl methacrylate, and
N,N-Diethylaminoethyl methacrylate.

The above-mentioned aromatic tertiary amine (b1) and the aliphatic tertiary amine (b2) can be used each in a single kind or can be used in a combination of two or more kinds.

Specifically, in the present invention, the aromatic tertiary amine (b1) can be desirably used. It is, however, more desired to use the aromatic tertiary amine (b1) and the aliphatic amine (b2) in combination from the standpoint of attaining a high polymerizability, completing the polymerization and curing by the irradiation with the light in a short period of time, attaining improved properties of the cured body and, further, decreasing the coloring when the cured body is exposed to ultraviolet rays such as sunlight. For instance, it is desired to use the aromatic tertiary amine (b1) and the aliphatic amine (b2) at a mass ratio of:
b1:b2=1:99 to 99:1
preferably, 40:60 to 80:20, and
more preferably, 50:50 to 70:30.

In the present invention, the tertiary amine compound (b) is, usually, used in an amount of 10 to 1,000 parts by mass and, more preferably, 50 to 500 parts by mass per 100 parts by mass of the photosensitizer 1(a).

(c) Aryliodonium Salts;

The aryliodonium salt (c) used in the present invention is a compound that has been known as a so-called acid generating agent, and has a property to form an acid derived from anions present in the molecules through the cleavage reaction upon being irradiated with the light. As the aryliodonium salt (c), the invention selects a compound that forms an acid that has an acid dissociation constant of not less than −3.0 in water (25° C.).

The aryliodonium salt is a diaryl compound which generates an acid (HX) through the cleavage reaction upon being irradiated with the light as represented by the following formula (2).

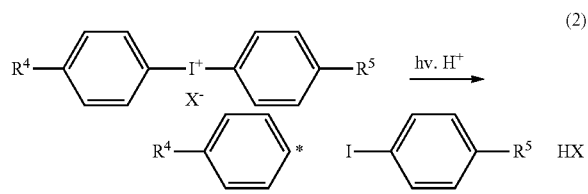

(2)

wherein, $R^4$ and $R^5$ are, independently from each other, hydrogen atoms or alkyl groups, X− is a counter anion of the aryliodonium salt, and HX is an acid generated by the cleavage reaction represented by the above formula (2).

Through the cleavage reaction represented by the above formula (2), the aryliodonium salt (c) used in the present invention generates an acid having a low acidity (acid dissociation constant in water of not less than −3.0).

That is, if the photocurable composition undergoes the polymerization reaction upon being irradiated with the active light, the photocurable composition containing the aryliodonium salt (c) together with the photosensitizer (a) and the tertiary amine compound (b), then there is generated an acid being derived from an aryl radical and a counter ion of the aryliodonium salt as represented by the following formula (3).

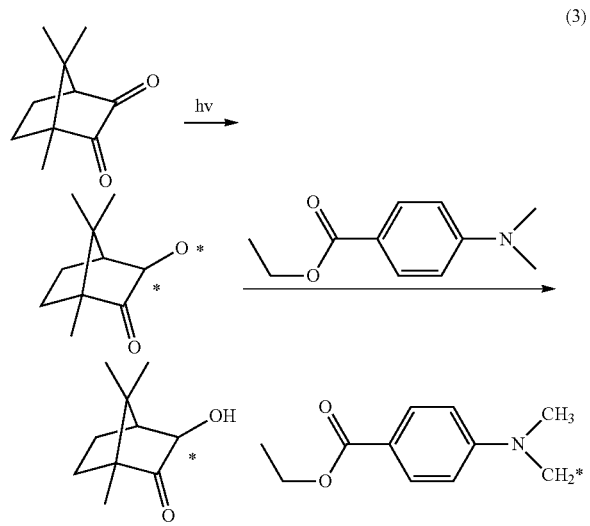

(3)

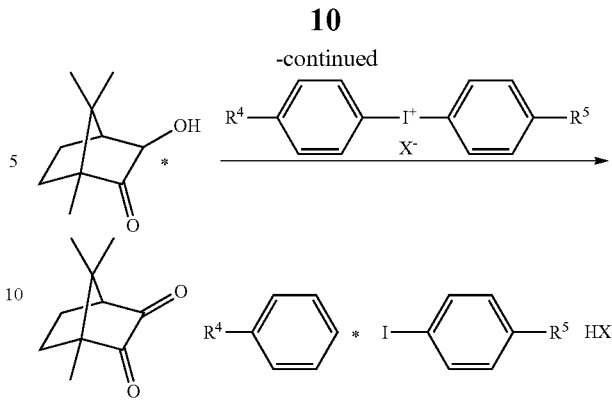

It is here considered that the higher the acidity of the acid that is generated, the more the polymerization is promoted. The patent document 1, for instance, is using a diphenyliodoniumhexafluorophosphate that generates an acid of a high acidity.

Here, when the polymerization initiator contains an amine compound and, specifically, a tertiary amine compound, the acid that has a high acidity undergoes the neutralization reaction with the tertiary amine compound and forms a salt thereof impairing, therefore, the property (reducing property or electron donating property) of the tertiary amine compound and, accordingly, seriously impairing the polymerizing activity.

In the present invention that uses the aryliodonium salt, on the other hand, the acid formed through the cleavage reaction has a low acidity effectively suppressing the neutralization reaction of the acid itself with the tertiary amine compound. Therefore, the aryl radical formed together with the acid acts effectively for initiating the polymerization and, therefore, very excellent polymerizing activity is exhibited.

As described above, the aryliodonium salt (c) used in the present invention generates an acid having a low acidity or, concretely, generates an acid having an acid dissociation constant in water (25° C.) of not less than −3.0 and, specifically, −2.0 to 10.0. By using the above compound in combination with the above-mentioned photosensitizer (a) and the tertiary amine compound (b), it is allowed to greatly improve the polymerizing activity by the active light.

For reference, described below are acid dissociation constants of various acids in water (25° C.).

HCL: −3.7
HBr: −4.1
$HNO_3$: −1.8
Chloroacetic acid: 2.9
Benzoic acid: 4.2
Phenol: 9.9

As the aryliodonium salt (c) that generates an acid having a low acidity, the invention can use a salt comprising any aryliodonium (cation) and counter anion so far as the acid that is generated has an acid dissociation constant that lies within the above-mentioned range. Preferably, there can be used the following cations and counter anions.

Examples of the Aryliodonium (Cation)

Diphenyliodonium,
Bis(p-chlorophenyl)iodonium,
Ditolyliodonium,
Bis(p-methoxyphenyl)iodonium,
Bis(p-tert-butylphenyl)iodonium,
p-Isopropylphenyl-p-methylphenyliodonium,
Bis(m-nitrophenyl)iodonium, p-Tert-butylphenylphenyliodonium,
p-Methoxyphenylphenyliodonium,
p-Octyloxyphenylphenyliodonium, and
p-Phenoxyphenylphenyliodonium.

Examples of the Counter Anion

Nitrate anion,
Acetate anion,
Chloroacetate anion,
Carboxylate anion, and
Phenolato anion.

In the invention, among the salts comprising the above aryliodonium and counter anion, there is particularly preferably used a diphenyliodonium-2-carboxylate monohydrate from the standpoint of easy availability and excellent curing rate.

The above aryliodonium salt (c) is used, usually, in an amount of 10 to 2,000 parts by mass, specifically, 20 to 1,000 parts by mass and, most preferably, 20 to 300 parts by mass per 100 parts by mass of the photosensitizer (a).

Further, the aryliodonium salt (c) does not work to neutralize the above-mentioned tertiary amine compound (b) to lower its property. Therefore, the aryliodonium salt (c) can be used in an amount relatively larger than the amount of the compound (b) to quicken the rate of curing when irradiated with the active light. For example, the aryliodonium salt (c) can be used in an amount of 10 to 80% by mass, specifically, 15 to 70% by mass and, more specifically, 30 to 60% by mass per the total amount of the tertiary amine compound (b) and the aryliodonium salt (c).

The photopolymerization initiator of the present invention comprising the photosensitizer (a), the tertiary amine compound (b) and the aryliodonium salt (c) is combined with the polymerizable monomer, and is used as the photocurable composition. In order to fully utilize its properties, in general, the photosensitizer (a) (specifically, α-diketon) in the photopolymerization initiator is used, desirably, in an amount of 0.01 to 10 parts by mass and specifically, 0.03 to 5 parts by mass per 100 parts by mass of the polymerizable monomer (specifically, the radically polymerizable monomer). From the standpoint of improving its stability in the environmental light, in particular, it is desired that the photosensitizer (a) is used in an amount of not more than 1 part by mass per 100 parts by mass of the polymerizable monomer. Therefore, when the photocurable composition is irradiated with the environmental light of such an intensity that is 0.3 mW/cm$^2$ on the surface of irradiation, a time of not shorter than 85 seconds and, specifically, not shorter than 90 seconds is required before it starts polymerizing, showing, therefore, excellent stability in the environmental light. In this case, too, the photocurable composition polymerizes and cures to a high degree when irradiated with the active light. When irradiated with the active light of such an intensity that is 640 to 650 mW/cm$^2$ on the surface of irradiation, therefore, the photocurable composition is completely polymerized and cured in about 20 seconds making it possible to obtain a cured body having, for example, a Vickers' hardness of not less than 30 and a bending strength of not less than 140 MPa though dependent upon the amount of the filler that is added.

<Photocurable Compositions>

Depending on the use, further, the photocurable composition containing the photopolymerization initiator of the present invention can be blended with suitable agents within a range in which they do not adversely affect the polymerizability by the active light or do not adversely affect stability in the environmental light, in addition to being blended with the polymerizable monomer and the photopolymerization initiator of the invention. For instance, the photocurable composition can be used for a variety of applications, such as dental materials, photoresist materials, printing and plate-making materials, hologram materials and the like. Depending on the use, therefore, the photocurable composition may be suitably blended with known blending agents. Specifically, the photocurable composition blended with the photopolymerization initiator of the present invention exhibits excellent polymerizing and curing properties by the active light and, besides, has an improved stability in the environmental light. Therefore, the photocurable composition of the invention is very useful as a composite resin for restoring the teeth.

Described below are the components with which the photocurable composition is blended.

Polymerizable Monomers;

As the polymerizable monomer in the invention, there can be used a radically polymerizable monomer as well as any other polymerizable monomers such as cationically polymerizable monomers like vinyl ether compound, epoxy compound, oxetane compound, aziridine compound, azetidine compound, episulfide compound, cyclic acetal, bicycloorthoester, spiroorthoester, spiroorthocarbonate and tetrahydrofuran. To utilize the property of the photopolymerizabe monomer of the invention to a sufficient degree, however, the radically polymerizable monomer is desirably used.

As the radically polymerizable monomer, there can be used the known radically polymerizable monomer without any limitation. Generally, however, a (meth)acrylate type polymerizable monomer is preferably used from the standpoint of curing rate and mechanical properties of the cured body. Specifically preferably, there is used a polyfunctional (meth)acrylate type polymerizable monomer having a plurality of polymerizable functional groups. As the polyfunctional (meth)acrylate type polymerizable monomer, there can be used the known ones without any specific limitation. Examples thereof that can be usually preferably used are described in (I) to (III) below.

(I) Bifunctionally Polymerizable Monomers;
(1-i) Aromatic Compound Type Bifunctionally Polymerizable Monomers.
2,2-Bis(methacryloyloxyphenyl)propane,
2,2-Bis[4-(3-methacryloyloxy)-2-hydroxypropyloxyphenyl]propane (hereinafter abbreviated as Bis-GMA),
2,2-Bis(4-methacryloyloxyphenyl)propane,
2,2-Bis(4-methacryloyloxypolyethoxyphenyl)propane (hereinafter abbreviated as D-2.6E),
2,2-Bis(4-methacryloyloxydiethoxyphenyl)propane,
2,2-Bis(4-methacryloyloxytetraethoxyphenyl)propane,
2,2-Bis(4-methacryloyloxypentaethoxyphenyl)propane,
2,2-Bis(4-methacryloyloxydipropyloxyphenyl)propane,
2(4-Methacryloyloxydiethoxyphenyl)-2-(4-methacryloyl oxytriethoxyphenyl)propane,
2(4-Methacryloyloxydipropyloxyphenyl)-2-(4-methacryloyloxytriethoxyphenyl)propane,
2,2-Bis(4-methacryloyloxypropyloxyphenyl)propane,
2,2-Bis(4-methacryloyloxyisopropyloxyphenyl)propane,
Acrylates corresponding to the above methacrylates, and
Diadducts obtained by adding a vinyl monomer having an OH group to the diisocyanate compounds having aromatic groups.

In the above examples, the diisocyanate compounds having the aromatic group are representatively the diisocyanatemethylbenzene and the 4,4'-diphenylmethanediisocyanate, and the vinyl monomers having the OH group are represented by the methacrylates such as 2-hydroxyethylmethacrylate, 2-hydroxypropylmethacrylate and 3-chloro-2-hydroxypropylmethacrylate or the acrylates corresponding to these methacrylates.

(1-ii) Aliphatic Compound Type Bifunctionally Polymerizable Monomers.

Ethylene glycol dimethacrylate,
Diethylene glycol dimethacrylate,
Triethylene glycol dimethacrylate (hereinafter abbreviated as 3G),
Tetraethylene glycol dimethacrylate,
Neopentyl glycol dimethacrylate,
1,3-Butanediol dimethacrylate,
1,4-Butanediol dimethacrylate,
1,6-Hexanediol dimethacrylate,
Acrylates corresponding to the above methacrylates,
1,2-Bis(3-methacryloyloxy-2-hydroxypropyloxy)ethyl, and
Diadducts obtained by adding a vinyl monomer having an OH group to the diisocyanate compounds.

In the above examples, the diisoyanate compounds can be represented by hexamethylene diisocyanate, trimethylhexamethylene diisocyanate diisocyanatemethylcyclohexane, isophorone diisocyanate and methylene bis(4-cyclohexylisocyanate), and the vinyl monomer having the OH group can be represented by the methacrylates such as 2-hydroxyethylmethacrylate, 2-hydroxypropylmethacrylate and 3-chloro-2-hydroxypropylmethacrylate or the acrylates corresponding to these methacrylates.

(II) Trifunctionally Polymerizable Monomers;
Methylolpropane trimethacrylate,
Trimethylolethane trimethacrylate,
Pentaerythritol trimethacrylate,
Trimethylolmethane trimethacrylate, and
Acrylates corresponding to the above methacrylates.

(III) Tetrafunctionally Polymerizable Monomers;
Pentaerythritol tetramethacrylate,
Pentaerythritol tetraacrylate, and
Diadducts obtained by adding glycidol dimethacrylate to the diisocyanate compounds.

As the diisocyanate compound, there can be exemplified diisocyanatemethylbenzene, diisocyanatemethylcyclohexane, isophorone diisocyanate, hexamethylene diisocyanate, trimethylhexamethylene diisocyanate, methylenebis(4-cyclohexyl isocyanate), 4,4-diphenylmethane diisocyanate and tolylene-2,4-diisocyanate.

These polyfunctional (meth)acrylate type polymerizable monomers may, as required, be used in a plurality of kinds in combination. As required, further, a monofunctional (meth)acrylate type monomer may be used.

The above radically polymerizable monomers can be used each in a single kind or in a combination of two or more kinds. As required, further, the radically polymerizable monomers can be mixed and polymerized with one or two or more kinds of the other polymerizable monomers than the above polymerizable monomers for easy polymerization or for adjusting the viscosity or any other properties. As the other polymerizable monomers, there can be exemplified the following compounds other than the above-mentioned cationically polymerizable monomers.

Fumaric acid esters such as monomethyl fumarate, diethyl fumarate and diphenyl fumarate;
Styrene or α-methylstyrene derivatives such as styrene, divinylbenzene, α-methylstyrene and α-methylstyrene dimer; and
Aryl compounds such as diaryl terephthalate, diaryl phthalate and diaryl diglycol carbonate.

Other Blending Agents;

As the blending agents to be suitably added in addition to the photopolymerization initiators and the polymerizable monomers, there can be representatively used fillers. Upon adding the fillers, the obtained cured body exhibits improved mechanical strength, etc.

As the fillers, there can be representatively used the following inorganic fillers.

Simple metals such as metals of the Groups I, II, III and IV of periodic table, and transition metals;
Oxides and composite oxides of the above metals; and
Metal salts such as fluorides of the above metals, carbonates, sulfates, silicates, hydroxides, chlorides, sulfides, phosphates, and composite products thereof.

Described below are the particularly preferably used inorganic fillers.

Metal oxides such as amorphous silica, quartz, alumina, titania, zirconia, barium oxide, yttrium oxide, lanthanum oxide and ytterbium oxide;
Silica type composite oxides such as silica-zirconia, silica-titania, silica-titania-barium oxide, and silica-titania-zirconia;
Glasses such as borosilicate glass, aluminosilicate glass and fluoroaluminosilicate glass;
Metal fluorides such as barium fluoride, strontium fluoride, yttrium fluoride, lanthanum fluoride and ytterbium fluoride;
Inorganic carbonates such as calcium carbonate, magnesium carbonate, strontium carbonate and barium carbonate; and
Metal sulfates such as magnesium sulfate and barium sulfate.

It is, further, allowable to use a granular organic-inorganic composite filler obtained by adding a polymerizable monomer to the inorganic fillers in advance, to obtain a paste-like mixture thereof followed by polymerization and, thereafter, by pulverization. Or it is, further, allowable to use an organic-inorganic composite filler obtained by adding a polymerizable monomer to the inorganic fillers in advance, and drying a mixture thereof followed by polymerization.

Further, the above fillers are treated with a surface-treating agent as represented by a silane coupling agent in order to improve affinity to the polymerizable monomer and, therefore, to improve the mechanical strength and waterproof property. As the silane coupling agent, there can be exemplified the following compounds.

Methyltrimethoxysilane,
Methyltriethoxysilane,
Methyltrichlorosilane,
Dimethyldichlorosilane
Trimethylchlorosilane,
Vinyltrichlorosilane,
Vinyltriethoxysilane,
Vinyltris(β-methoxyethoxy) silane,
γ-Methacryloyloxypropyltrimethoxysilane,
γ-Chloropropyltrimethoxysilane,
γ-Glycidoxypropyltrimethoxysilane, and
Hexamethyldisilazane.

When the photocurable composition is used as a dental composite resin, it is desired to use, among the above-mentioned fillers, the silica-zirconia, silica-titania, silica-titania-barium oxide, silica-titania-zirconia, or the surface-treated product thereof and, most desirably, the silica-zirconia from the standpoint of attaining a strong X-ray contrast-enhancing property.

The above-mentioned fillers can be used each in a single kind or can be used in a combination of two or more kinds. Depending on the kind of use of the photocurable composition, further, there is used a filler having a suitable refractive index. Depending on the kind of use, furthermore, the filler is used with its grain size being suitably adjusted. For example, when the photocurable composition is used as the dental composite resin, in general, the filler is adjusted to have a refractive index of about 1.4 to about 1.7 and a grain size of about 0.01 to 100 μm and, specifically, about 0.01 to about 5 μm.

When used as the dental composite resin, furthermore, it is desired to use the filler that has, among other shapes, a spherical shape so that the cured body that is obtained exhibits enhanced surface luster and that the photocurable composition could serve as an excellent dental restorative.

The amount of the filler that is added may be suitably determined depending on the object of use and by taking into consideration the viscosity (operability) of when it is mixed with the polymerizable monomer and the mechanical properties of the cured body. When used as the dental composite resin, however, it is desired that the filler is used in an amount in a range of 50 to 1500 parts by mass and, specifically, 70 to 1000 parts by mass per 100 parts by mass of the above-mentioned polymerizable monomer.

The photocurable composition blended with the photopolymerization initiator of the present invention can be, further, blended with a known polymerization initiator such as an organic peroxide in a range in which it does not impair the polymerizability and curability by the active light or does not impair the stability in the environmental light.

To the photocurable composition blended with the photopolymerization initiator of the present invention, it is also allowable to add water, organic solvent and a thickener depending on the object and in a range in which they do not impair the properties of the photocurable composition. As the organic solvent, there can be exemplified hexane, heptane, octane, toluene, dichloromethane, methanol, ethanol and ethyl acetate while as the thickener, there can be exemplified high molecular compounds such as polyvinyl pyrrolidone, carboxymethyl cellulose and polyvinylalcohol, as well as highly dispersible silica.

The photocurable composition blended with the photopolymerization initiator of the present invention can be cured by using a known light source which may be the same as the one used for curing the α-diketone type photopolymerization initiators. Here, however, in order to utilize the feature of the photopolymerization initiator of the present invention that the photocurable composition remains relatively stable despite it is irradiated with the light of a low intensity but is quickly cured when it is irradiated with the light of a high intensity which is not lower than a predetermined level, there can be used, without any limitation, a source of visible light, such as carbon arc, xenon lamp, metal halide lamp, tungsten lamp, LED, halogen lamp, helium-cadmium laser or argon laser. The irradiation time, however, differs depending on the wavelength of the light source, intensity of the light, shape and material of the cured body. Therefore, the irradiation time should be determined in advance by conducting preliminary experiments.

As described already, the photocurable composition has excellent stability in the environmental light and cures excellently when it is irradiated with the active light. Therefore, the photocurable composition can be favorably used as a dental composite resin for restoring the teeth that are broken by decay.

In order to be in match with the color tone of the teeth, the composite resin may be, further, blended, in addition to the above-mentioned components, with pigment, fluorescent pigment, dye, or ultraviolet-ray absorber for preventing discoloration caused by ultraviolet rays, and may be, further, blended with known additives as components of the dental composite resin within a range in which they do not affect the effects of the present invention.

The photopolymerizable composite resin is prepared by weighing out in predetermined amounts the components that are to be blended and kneading them together until the mixture thereof becomes homogeneous while shutting off the light.

EXAMPLES

The invention will now be concretely described by way of Examples and Comparative Examples to which only, however, the technical idea of the invention is in no way limited. Described below are the photosensitizer (a), tertiary amine compounds (b), aryliodonium salts (c), polymerizable monomers and various additives that are used in Examples and Comparative Examples of the present invention.

[Photosensitizer (a)]
 CQ; Camphorquinone

[Tertiary Amine Compounds (b)]
 DMBE;
 Ethyl p-dimethylaminobenzoate
 DMPT;
 N,N-Dimethyl-p-toluidine
 MDEOA;
 N-Methyldiethanolamine

[Aryliodonium Salts (c)]
(Numerals in parentheses represent acid dissociation constants in water at 25° C.)
 DPICH;
 Diphenyliodonium-2-carboxylate monohydrate (4.2)
 DPIN;
 Diphenyliodonium nitrate (−1.8)
 DPIC;
 Diphenyliodonium chloride (−3.7)
 DPIB;
 Diphenyliodonium bromide (−4.1)

[Polymerizable Monomers]
 Bis-GMA;
 2,2-Bis[4-(3-methacryloyloxy-2-hydroxypropyloxy)phenyl]propane
 3G;
 Triethylene glycol dimethacrylate
 UDMA;
 1,6-Bis(methacrylethyloxycarbonylamino)Trimethylhexane D-2.6E;
Compound represented by the following formula,

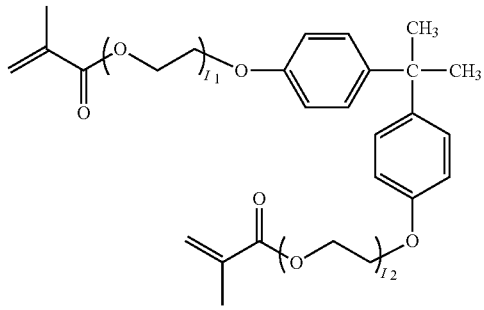

(4)

A mixture whose $(I_1+I_2)$ on the average is 2.6.
[Fillers]
E-1;
Spherical silica-zirconia (whose surface is treated with γ-methacryloyloxypropyltrimethoxysilane,
average
  grain size; 0.5 μm)
E-2;
Spherical silica-titania (whose surface is treated with γ-methacryloyloxypropyltrimethoxysilane,
average
  grain size; 0.08 μm)
[Other Components]
HQME;
Hydroquinonemonomethyl ether Described below are the method of preparing a photopolymerization type composite resin which is one of the use of the photocurable composition, and the methods of measuring the curing properties (stability in the environmental light, curability, hardness) and mechanical strengths of the cured bodies.

(1) Method of Preparing the Photopolymerization Type Composite Resin

The photopolymerization type composite resin was prepared by blending the polymerizable monomer with the photopolymerization initiator, filler and other blending components in predetermined amounts, and stirring and defoaming the mixture thereof in the red light.

(2) Hardness (Vickers' Hardness) of the Cured Body

By using a dental light irradiator described below, the cured body was measured for its hardness by the method described below. That is, a mold made of a polytetrafluoroethylene and having a hole of 6 mmφ×1.0 mm was filled with the photocurable composition and to which a polypropylene film was press-contacted. The Tokuso Power Light was used as the dental light irradiator; i.e., the irradiator was closely contacted to the polypropylene film, and the light was irradiated for 20 seconds to prepare a cured body. By using a microhardness tester (Model MHT-1 manufactured by MATSUZAWA Co., Ltd.), a dent was formed in the thus obtained cured body by pressing a Vickers' indentater thereon with a load of 100 gf and maintaining the load for 30 seconds. The hardness of the cured body was found from the length of a diagonal line of the dent {Tokuso Power Light: light output density of 700 mW/cm², light intensity on the irradiated surface of 640 to 650 mW/cm², light source was a halogen lamp, Tokuyama Dental Corporation}.

(3) Bending Strength

A stainless steel frame was filled with the photocurable composition and to which the polypropylene was press-contacted. In this state, the photocurable composition was irradiated on one surface thereof with the light from the Tokuso Power Light that was closely contacted to the polypropylene for 20 seconds×three times such that the entire photocurable composition was irradiated with the light. The photocurable composition was, thereafter, irradiated on the opposite surface thereof with the light from the Tokuso Power Light that was closely contacted to the polypropylene for 20 seconds×three times, and a cured body was obtained. By using a water-proof polishing paper #800, the cured body was shaped into a square pole measuring 2×2×25 mm. The thus shaped test piece was fitted to a tester (Autograph AG5000D manufactured by Shimadzu Corporation) to measure a three-point bending breaking strength under the conditions of a distance between fulcrums of 20 mm and a crosshead speed of 1 mm/min.

(4) Testing the Stability in the Environmental Light

The distance between the light source and the sample was so set that the light intensity was 10,000 lux on the surface of the sample paste-like photocurable composition. The Dental Light (light source: halogen lamp, manufactured by TAKARA BELMONT CORPORATION) was used as the light source, and the distance between the sample and the light source was so set that the light intensity became the above intensity as measured by using an illuminometer. The light intensity was 0.3 mW/cm² on the irradiated surface. 0.03 Grams of the sample photocurable composition prepared above was weighed out on the polypropylene film and was irradiated with the light from the Dental Light for a predetermined period of time. The sample was, thereafter, crushed and the time was measured until the interior of the sample started solidifying. The irradiation time was 5 seconds each. The longer the time, the more excellent the stability in the environmental light and, therefore, more time for favorably conducting the operation.

The illuminometer was the Digital Lux Meter FLX-1330 manufactured by Tokyo Garasu Kikai Corporation. The illuminometer has a sensitivity at 400 to 700 nm.

Example 1

The components of the following recipe were mixed together in a dark place to obtain a homogeneous solution of a photocurable composition.
Polymerizable monomers (100 parts by mass);
  D-2.6E: 70 parts by mass
  3G: 25 parts by mass
  UDMA: 5 parts by mass
Photopolymerization Initiators (1.2 Parts by Mass);
  CQ: 0.3 parts by mass
  DMBE: 0.5 parts by mass
  DPICH: 0.4 parts by mass The cured body prepared from the above solution was evaluated for its Vickers' hardness under the above-mentioned conditions. The result was as shown in Table 1.

Examples 2 to 7, Comparative Examples 1 to 6

Solutions were prepared in the same manner as in Example 1 but using the photopolymerization initiators in combinations as described in Table 1. Cured bodies prepared from the above solutions under the above-mentioned conditions were evaluated for their Vickers' hardnesses. The results were as shown in Table 1.

TABLE 1

| | Photopolymerization initiator | | | Acid dissociation constant of the generated acid in water (25° C.) | Vickers' hardness |
|---|---|---|---|---|---|
| | Photosensitizer (a) | Tertiary amine compound (b) | Diaryliodonium salt (c) | | |
| Ex. 1 | CQ 0.3 | DMBE 0.5 | DPICH 0.4 | 4.2 | 18 |
| Ex. 2 | CQ 0.3 | DMBE 0.3/MDEOA 0.2 | DPICH 0.4 | 4.2 | 21 |
| Ex. 3 | CQ 0.3 | DMBE 0.5 | DPICH 0.2 | 4.2 | 14 |
| Ex. 4 | CQ 0.3 | DMBE 0.5 | DPIN 0.4 | −1.8 | 14 |
| Ex. 5 | CQ 0.3 | DMBE 0.3/MDEOA 0.2 | DPIN 0.4 | −1.8 | 17 |
| Ex. 6 | CQ 0.3 | DMPT 0.5 | DPICH 0.4 | 4.2 | 17 |
| Ex. 7 | CQ 0.3 | DMPT 0.3/MDEOA 0.2 | DPICH 0.4 | 4.2 | 20 |
| Comp. Ex. 1 | CQ 0.3 | DMBE 0.5 | 0 | — | 7 |
| Comp. Ex. 2 | CQ 0.3 | DMBE 0.3/MDEOA 0.2 | 0 | — | 7 |
| Comp. Ex. 3 | CQ 0.3 | 0 | DPICH 0.4 | 4.2 | <5 |
| Comp. Ex. 4 | 0 | DMBE 0.5 | DPICH 0.4 | 4.2 | <5 |
| Comp. Ex. 5 | CQ 0.3 | DMBE 0.5 | DPIB 0.4 | −4.1 | 8 |
| Comp. Ex. 6 | CQ 0.3 | DMBE 0.5 | DPIC 0.4 | −3.7 | 9 |

As demonstrated by Examples 1 to 7, high Vickers' hardnesses were exhibited by the cured bodies that were obtained from the solutions comprising in combination the photosensitizer (a), the tertiary amine compound (b) and the aryliodonium salt (c) that generated, through the cleavage reaction, the acid having an acid dissociation constant of not less than −3.0 in water (25° C.).

Comparative Examples 1 and 2 were the cases that were not blended with the aryliodonium salt (c) that was one of the essential components of the photopolymerization initiator of the present invention. In these cases, the Vickers' hardnesses were lower than those of Examples that were blended with the aryliodonium salt (c).

Comparative Example 3 was the case that was not blended with the tertiary amine compound (b), and Comparative Example 4 was the case that was not blended with the photosensitizer (a). In these cases, the Vickers' hardnesses were further lower than those of the cases of when not blended with the aryliodonium salt (c).

Comparative Examples 5 and 6 were the cases that used the aryliodonium salt that, through the cleavage reaction, generated the acid having an acid dissociation constant of less than −3.0 in water (25° C.). In these cases, the Vickers' hardnesses were higher than that of Comparative Example 1 but were lower than those of Examples.

Example 8

A paste-like composition was prepared according to the following recipe.
Polymerizable Monomers (100 Parts by Mass);
  D-2.6E: 70 parts by mass
  3G: 25 parts by mass
  UDMA: 5 parts by mass
Fillers (400 Parts by Mass);
  E-1: 160 parts by mass
  E-2: 240 parts by mass
Polymerization Inhibitor (HQME): 0.15 Parts by Mass
To the above paste-like composition was, further, added a photopolymerization initiator of a composition shown in Table 2 to obtain a photopolymerization type composite resin which was then evaluated for its Vickers' hardness, bending strength and stability in the environmental light. The results were as shown in Table 2.

Examples 9 to 17, Comparative Examples 7 to 13

Photopolymerization type composite resins were prepared in the same manner as in Example 8 but using the photopolymerization initiators in combinations as described in Table 2. The photopolymerization type composite resins were evaluated for their Vickers' hardnesses, bending strengths and stabilities in the environmental light under the above-mentioned conditions. The results were as shown in Table 2.

TABLE 2

| | Photopolymerization initiator | | | Acid dissociation constant of the generated acid in water (25° C.) | Vickers' hardness | Bending strength [MPa] | Stability in the environmental light [sec.] |
|---|---|---|---|---|---|---|---|
| | Photosensitizer (a) | Tertiary amine compound (b) | Diaryliodonium salt (c) | | | | |
| Ex. 8 | CQ 0.3 | DMBE 0.5 | DPICH 0.07 | 4.2 | 37 | 148 | 105 |
| Ex. 9 | CQ 0.3 | DMBE 0.5 | DPICH 0.2 | 4.2 | 40 | 152 | 100 |
| Ex. 10 | CQ 0.3 | DMBE 0.5 | DPICH 0.4 | 4.2 | 48 | 165 | 95 |
| Ex. 11 | CQ 0.3 | DMBE 0.5 | DPICH 0.6 | 4.2 | 49 | 167 | 95 |
| Ex. 12 | CQ 0.3 | DMBE 0.5 | DPICH 0.8 | 4.2 | 48 | 165 | 90 |
| Ex. 13 | CQ 0.3 | DMBE 0.3/MDEOA 0.2 | DPICH 0.4 | 4.2 | 50 | 170 | 90 |
| Ex. 1.4 | CQ 0.3 | DMBE 0.5 | DPIN 0.4 | −1.8 | 40 | 153 | 100 |
| Ex. 15 | CQ 0.3 | DMBE 0.3/MDEOA 0.2 | DPIN 0.4 | −1.8 | 46 | 163 | 95 |

TABLE 2-continued

| | Photopolymerization initiator | | | | | | |
|---|---|---|---|---|---|---|---|
| | Photosensitizer (a) | Tertiary amine compound (b) | Diaryliodonium salt (c) | Acid dissociation constant of the generated acid in water (25° C.) | Vickers' hardness | Bending strength [MPa] | Stability in the environmental light [sec.] |
| Ex. 16 | CQ 0.3 | DMPT 0.5 | DPICH 0.4 | 4.2 | 46 | 163 | 95 |
| Ex. 17 | CQ 0.3 | DMPT 0.3/ MDEOA 0.2 | DPICH 0.4 | 4.2 | 48 | 168 | 90 |
| Comp. Ex. 7 | CQ 0.3 | DMBE 0.5 | 0 | — | 22 | 120 | 105 |
| Comp. Ex. 8 | CQ 0.3 | DMBE 0.3/ MDEOA 0.2 | 0 | — | 24 | 122 | 100 |
| Comp. Ex. 9 | CQ 0.6 | DMBE 1.0 | 0 | — | 28 | 128 | 55 |
| Comp. Ex. 10 | CQ 0.3 | 0 | DPICH 0.4 | 4.2 | <5 | <80 | 180< |
| Comp. Ex. 11 | 0 | DMBE 0.5 | DPICH 0.4 | 4.2 | <5 | <80 | 180< |
| Comp. Ex. 12 | CQ 0.3 | DMBE 0.5 | DPIB 0.4 | −4.1 | 26 | 125 | 100 |
| Comp. Ex. 13 | CQ 0.3 | DMBE 0.5 | DPIC 0.4 | −3.7 | 28 | 127 | 100 |

As will be understood from the results of Examples 8 to 17, the cured bodies using the photopolymerization initiators of the present invention exhibited high Vickers' hardnesses and bending strengths.

Comparative Examples 7 and 8 were the cases that were not blended with the aryliodonium salt (c) that generated, through the cleavage reaction, the acid having an acid dissociation constant of not less than −3.0 in water (25° C.). In these cases, the Vickers' hardnesses were lower than those of Examples 8 to 17.

Comparative Example 9 was the case that was the same as Comparative Example 7 but to which were added in increased amounts the CQ which was the photosensitizer and the DMBE which was the tertiary amine compound. In this case, the Vickers' hardness and the bending strength were higher, but the stability in the environmental light was lower, than those of Comparative Example 7. As described above, simply adding the photosensitizer and the tertiary amine compound in increased amounts does not help obtain the photopolymerization type composite resin that satisfies both the curability and the stability in the environmental light.

Comparative Example 10 was the case that was not blended with the tertiary amine compound (b) while Comparative Example 11 was the case that was not blended with the photosensitizer (a). In these cases, the Vickers' hardnesses and the bending strengths were even lower than those of when the aryliodonium salt (c) was not used.

Comparative Examples 12 and 13 were the cases blended with the aryliodonium salt that generated, through the cleavage reaction, the acid having an acid dissociation constant of less than −3.0 in water (25° C.). In these cases, the Vickers' hardnesses and the bending strengths were higher than those of Comparative Example 7 but were lower than those of Examples 8 to 17.

Example 18

A paste-like composition was prepared according to the following recipe.
Polymerizable Monomers (100 Parts by Mass);
  Bis-GMA: 60 parts by mass
  3G: 40 parts by mass
FILLERS (150 parts by mass);
  E-1: 105 parts by mass
  E-2: 45 parts by mass
Polymerization Inhibitor (HQME): 0.15 Parts by Mass To the above paste-like composition was further added a photopolymerization initiator of a compositions shown in Table 3 to obtain a photopolymerization type composite resin which was then evaluated for its Vickers' hardness, bending strength and stability in the environmental light. The results were as shown in Table 3.

Examples 19 to 27, Comparative Examples 14 to 20

Photopolymerization type composite resins were prepared in the same manner as in Example 18 but using the photopolymerization initiators in combinations as described in Table 3. The photopolymerization type composite resins were evaluated for their Vickers' hardnesses, bending strengths and stabilities in the environmental light under the above-mentioned conditions. The results were as shown in Table 3.

TABLE 3

| | Photopolymerization initiator | | | | | | |
|---|---|---|---|---|---|---|---|
| | Photosensitizer (a) | Tertiary amine compound (b) | Diaryliodonium salt (c) | Acid dissociation constant of the generated acid in water (25° C.) | Vickers' hardness | Bending strength [MPa] | Stability in the environmental light [sec.] |
| Ex. 18 | CQ 0.3 | DMBE 0.5 | DPICH 0.07 | 4.2 | 33 | 143 | 95 |
| Ex. 19 | CQ 0.3 | DMBE 0.5 | DPICH 0.2 | 4.2 | 37 | 147 | 95 |
| Ex. 20 | CQ 0.3 | DMBE 0.5 | DPICH 0.4 | 4.2 | 40 | 155 | 95 |
| Ex. 21 | CQ 0.3 | DMBE 0.5 | DPICH 0.6 | 4.2 | 41 | 155 | 95 |

TABLE 3-continued

| | Photopolymerization initiator | | | | | | |
|---|---|---|---|---|---|---|---|
| | Photosensitizer (a) | Tertiary amine compound (b) | Diaryliodonium salt (c) | Acid dissociation constant of the generated acid in water (25° C.) | Vickers' hardness | Bending strength [MPa] | Stability in the environmental light [sec.] |
| Ex. 22 | CQ 0.3 | DMBE 0.5 | DPICH 0.8 | 4.2 | 40 | 153 | 90 |
| Ex. 23 | CQ 0.3 | DMBE 0.3/ MDEOA 0.2 | DPICH 0.4 | 4.2 | 45 | 161 | 85 |
| Ex. 24 | CQ 0.3 | DMBE 0.5 | DPIN 0.4 | −1.8 | 35 | 145 | 95 |
| Ex. 25 | CQ 0.3 | DMBE 0.3/ MDEOA 0.2 | DPIN 0.4 | −1.8 | 39 | 152 | 90 |
| Ex. 26 | CQ 0.3 | DMPT 0.5 | DPICH 0.4 | 4.2 | 38 | 152 | 95 |
| Ex. 27 | CQ 0.3 | DMPT 0.3/ MDEOA 0.2 | DPICH 0.4 | 4.2 | 43 | 158 | 90 |
| Comp. Ex. 14 | CQ 0.3 | DMBE 0.5 | 0 | — | 18 | 110 | 100 |
| Comp. Ex. 15 | CQ 0.3 | DMBE 0.3/ MDEOA 0.2 | 0 | — | 20 | 115 | 95 |
| Comp. Ex. 16 | CQ 0.6 | DMBE 1.0 | 0 | — | 25 | 123 | 50 |
| Comp. Ex. 17 | CQ 0.3 | 0 | DPICH 0.4 | 4.2 | <5 | <80 | 180< |
| Comp. Ex. 18 | 0 | DMBE 0.5 | DPICH 0.4 | 4.2 | <5 | <80 | 180< |
| Comp. Ex. 19 | CQ 0.3 | DMBE 0.5 | DPIB 0.4 | −4.1 | 23 | 122 | 95 |
| Comp. Ex. 20 | CQ 0.3 | DMBE 0.5 | DPIC 0.4 | −3.7 | 26 | 125 | 95 |

As demonstrated by Examples 18 to 27, the cured bodies using the photopolymerization initiators of the present invention exhibited high Vickers' hardnesses and bending strengths.

Comparative Examples 14 and 15 were the cases that were not blended with the aryliodonium salt (c) that generated, through the cleavage reaction, the acid having an acid dissociation constant of not less than −3.0 in water (25° C.). In these cases, the Vickers' hardnesses were lower than those of Examples 18 to 27.

Comparative Example 16 was the case that was the same as Comparative Example 14 but to which were added in increased amounts the CQ which was the photosensitizer and the DMBE which was the tertiary amine compound. In this case, the Vickers' hardness and the bending strength were higher, but the stability in the environmental light was lower, than those of Comparative Example 14.

As described above, simply adding the photosensitizer and the tertiary amine compound in increased amounts does not help obtain the photopolymerization type composite resin that satisfies both the curability and the stability in the environmental light.

Comparative Example 17 was the case that was not blended with the tertiary amine compound (b) while Comparative Example 18 was the case that was not blended with the photosensitizer (a). In these cases, the Vickers' hardnesses and the bending strengths were even lower than those of when the aryliodonium salt (c) was not used.

Comparative Examples 19 and 20 were the cases that were blended with the aryliodonium salt that generated, through the cleavage reaction, the acid having an acid dissociation constant of less than −3.0 in water (25° C.). In these cases, the Vickers' hardnesses and the bending strengths were higher than those of Comparative Example 14 but were lower than those of Examples 18 to 27.

The invention claimed is:

1. A photocurable composition including:
   a photopolymerization initiator containing (a) a photosensitizer, (b) a tertiary amine compound and (c) an aryliodonium salt; and
   a polymerizable monomer;
   wherein said aryliodonium salt (c) in said photopolymerization initiator is: (i) diphenyliodonium-2-carboxylate monohydrate; or (ii) a salt that comprises an aryliodonium cation and a counter anion selected from a group consisting of a nitrate anion, an acetate anion, a chloroacetate anion, a carboxylate anion and a phenolate anion, and
   wherein said aryliodonium salt (c) is the one that generates an acid having a dissociation constant of −2.0 to 10.0 in water of 25° C.

2. The photocurable composition according to claim 1, wherein said photopolymerization initiator is added in such an amount that the amount of said photosensitizer (a) in said photopolymerization initiator is 0.01 to 10 parts by mass per 100 parts by mass of said polymerizable monomer.

3. The photocurable composition according to claim 1, wherein said photocurable composition, further, includes a filler, and is used as a dental composite resin.

4. The photocurable composition according to claim 1, wherein said aryliodonium salt (c) is a diphenyliodonium-2-carboxylate monohydrate.

5. The photocurable composition according to claim 1, wherein said photosensitizer (a) is an α-diketone.

6. The photocurable composition according to claim 1, wherein said tertiary amine compound (b) includes an aromatic tertiary amine (b1).

7. The photocurable composition according to claim 6, wherein said tertiary amine compound (b) includes the aromatic tertiary amine (b1) and an aliphatic tertiary amine (b2).

8. The photocurable composition according to claim 1, wherein said tertiary amine compound (b) is contained in an amount of 10 to 1000 parts by mass and said aryliodonium salt (c) is contained in an amount of 10 to 2000 parts by mass per 100 parts by mass of said photosensitizer (a).

9. The photocurable composition according to claim 8, wherein said aryliodonium salt (c) is contained in an amount of 10 to 80% by mass on the basis of the total amount of said tertiary amine compound (b) and said aryliodonium salt (c).

* * * * *